(12) United States Patent
Funch-Nielsen

(10) Patent No.: US 11,733,231 B2
(45) Date of Patent: Aug. 22, 2023

(54) BREATH-CONDENSATE ANALYSER

(71) Applicant: Exhalation Technology Limited, Cambridge (GB)

(72) Inventor: Helle Funch-Nielsen, Hørsholm (DK)

(73) Assignee: Exhalation Technology Limited, Cambridge (GB)

( * ) Notice: Subject to any disclaimer, the term of this patent is extended or adjusted under 35 U.S.C. 154(b) by 127 days.

(21) Appl. No.: 16/494,979

(22) PCT Filed: Mar. 20, 2018

(86) PCT No.: PCT/GB2018/050720
§ 371 (c)(1),
(2) Date: Sep. 17, 2019

(87) PCT Pub. No.: WO2018/172760
PCT Pub. Date: Sep. 27, 2018

(65) Prior Publication Data
US 2020/0033323 A1 Jan. 30, 2020

(30) Foreign Application Priority Data

Mar. 20, 2017 (GB) .................................... 1704367

(51) Int. Cl.
*G01N 33/497* (2006.01)
*A61B 5/08* (2006.01)
(Continued)

(52) U.S. Cl.
CPC .......... *G01N 33/497* (2013.01); *A61B 5/082* (2013.01); *A61B 5/087* (2013.01); *A61B 5/097* (2013.01);
(Continued)

(58) Field of Classification Search
CPC ......... G01N 2001/4033; G01N 25/142; G01N 33/497; G01N 2033/4975;
(Continued)

(56) References Cited

U.S. PATENT DOCUMENTS 7,144,741 B2 12/2006 Rothe et al.
9,968,281 B2 5/2018 Bulbrook
(Continued)

FOREIGN PATENT DOCUMENTS

DE 199 51 204 A1 5/2001
DE 101 37 565 A1 3/2003
(Continued)

OTHER PUBLICATIONS

Search Report for corresponding Patent Application No. GB1704367.0 dated Jan. 29, 2018.
(Continued)

*Primary Examiner* — Benjamin R Schmitt
(74) *Attorney, Agent, or Firm* — Renner, Otto, Boisselle & Sklar, LLP

(57) ABSTRACT

An analyser for collecting and analysing a breath condensate is disclosed. The analyser comprises a housing and a cartridge device (10). The device comprises a condensation zone (12) to condense exhaled breath from a subject and cooling means operably connected to the condensation zone (12). The device includes further discrete regions (13) for detection of analyte and measurement of analyte. The condensation zone (12) has a fluid exit connecting the condensation zone (12) to the discrete regions (13). The analyser includes a mouthpiece which is provided with a plurality of chambers configured to cause a change of 90° in the direction of the exhaled breath in order to trap saliva aerosols.

18 Claims, 14 Drawing Sheets

(51) Int. Cl.
*A61B 5/087* (2006.01)
*A61B 5/097* (2006.01)
*A61B 10/00* (2006.01)
*G01N 1/40* (2006.01)
*G01N 25/14* (2006.01)

(52) U.S. Cl.
CPC .... *A61B 2010/0087* (2013.01); *G01N 25/142* (2013.01); *G01N 2001/4033* (2013.01); *G01N 2291/0253* (2013.01)

(58) Field of Classification Search
CPC .............. G01N 2291/0253; A61B 5/082; A61B 5/087; A61B 5/097; A61B 2010/0087
See application file for complete search history.

(56) References Cited

U.S. PATENT DOCUMENTS

| | | |
|---|---|---|
| 2005/0130226 A1 | 6/2005 | Ahn et al. |
| 2007/0173731 A1 | 7/2007 | Meka et al. |
| 2008/0061238 A1 | 3/2008 | Hok et al. |
| 2008/0214947 A1 | 9/2008 | Hunt et al. |
| 2010/0241019 A1 | 9/2010 | Varga et al. |
| 2010/0268106 A1 | 10/2010 | Johnson et al. |
| 2014/0366609 A1* | 12/2014 | Beck ................. B29C 65/46 73/23.3 |

FOREIGN PATENT DOCUMENTS

| | | |
|---|---|---|
| DE | 102015203719 A1 | 9/2016 |
| EP | 2 173 250 A1 | 4/2010 |
| WO | 97/35519 A1 | 10/1997 |
| WO | 2008/021617 A1 | 2/2008 |
| WO | 2008/022183 A1 | 2/2008 |
| WO | 2015/015201 A1 | 2/2015 |

OTHER PUBLICATIONS

International Search Report and Written Opinion for corresponding Patent Application No. PCT/GB2018/050720 dated Aug. 31, 2018.
International Search Report and Written Opinion for Patent Application No. PCT/GB2018/050721 dated Jul. 10, 2018.
Search Report for Patent Application No. GB1704367.0 dated Jan. 29, 2018.
Office Action for U.S. Appl. No. 16/494,981 dated Mar. 2, 2022.

* cited by examiner

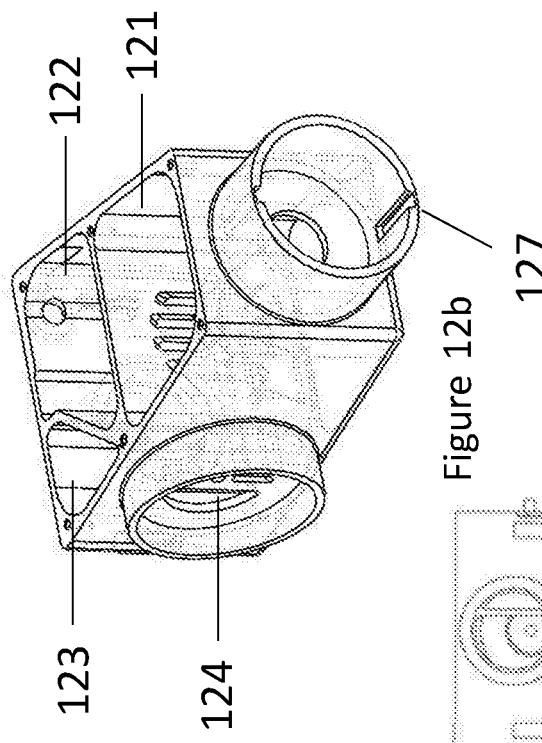
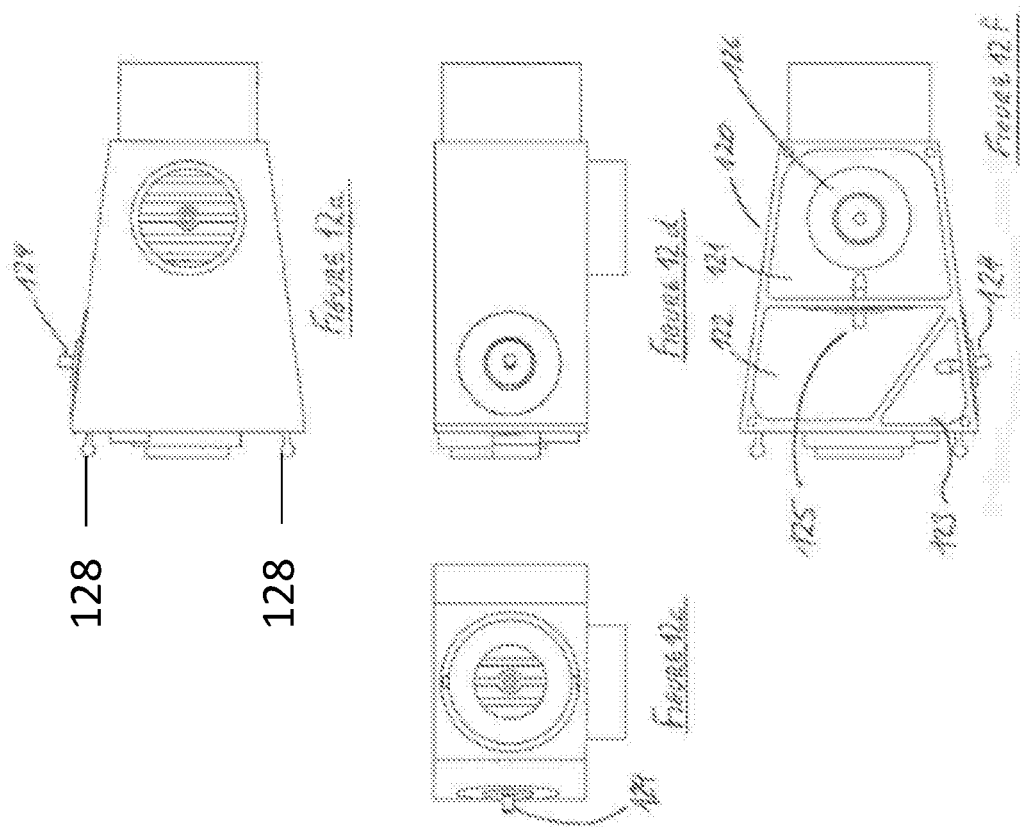

BREATH-CONDENSATE ANALYSER

FIELD OF THE INVENTION

The present invention relates to a device for use in analysing exhaled mammalian breath, especially that of a human, but also of animals such as horses, dogs, etc. The device is particularly for use in analysing alveolar air.

BACKGROUND OF THE INVENTION

In a previous application, EP2173250, assigned to the Applicant, a device is described which allows efficient collection of exhaled breath, and in particular collection with a minimal loss of volatile components, which would introduce error into subsequent analyses. Once the breath sample is condensed, it is then made available for analysis. However, analysis needs to be done separately from the device, which means the sample constituents can change in the meantime, affecting the results obtained.

Prior art document DE199 51 204 describes a method of condensing exhaled breath until a predetermined volume of sample is obtained. The sample thus obtained is moved from the storage zone to a detection zone. However, the methodology includes a delay between the collection and detection so that any inherent instabilities in the sample will affect the final concentrations determined. For example, the sample has sufficient time to dry out, short-lived species may decompose and there is a risk of contamination from outside sources.

DE 101 375 65 addresses the problems partially through the provision of a closed cassette for measurement of breath condensate. Within the device, buffer solutions and/or sensor calibration solutions are included. However, some of the liquid reagents used have a limited shelf life. Moreover, the operator is required to perform several manual steps, often using said liquid reagents, which can lead to delay and potential errors.

SUMMARY OF THE INVENTION

In a first, broad, independent aspect, there is provided an analyser for collecting and analysing a breath condensate, the analyser comprising a housing, the housing having a cooling means and, further, retaining a cartridge device comprising a condensation zone to condense exhaled breath from a subject, the cooling means being in cooling relationship with the condensation zone, the device including one or more further discrete regions for detection of analyte and measurement of analyte, the cartridge device further comprising a fluid path connecting the condensation zone to the or each discrete region, the housing including a mouth-piece having an entry port to enable a user to breathe into the mouth-piece, the mouth-piece comprising one or more fluid passages to direct breath entering the mouth-piece into the condensation zone.

This configuration is particularly advantageous because the integrated nature of the analyser allows for minimal interventions from an operator and therefore increases the accuracy and the reliability of the analysis produced and only a single exhaled breath condensate is required. This configuration also minimises the risk of any cross-contamination or loss of sample occurring. The spatial separation of a region from another region allows for regions to be held at different temperatures and conditions, and as the condensate is provided with a natural flow path into channels and sensing zones of the discrete regions there is no need for interference from an operator, thereby removing one of the biggest sources of inaccuracy: user error when performing manual tasks.

Advantageously, the cartridge device is removably attachable to the housing, enabling a used cartridge device to be replaced.

The housing preferably comprises a heating means to heat a reaction zone which itself forms part of the cartridge. The heating means is further preferably arranged in the housing or as part of the cartridge. There is optionally an electrical connection between the housing and the cartridge. The heating means may be an Ohmic heater.

Heating and cooling means enable both condensation to a breath condensate film and subsequently performance of enzymatic assays upon the film. Furthermore, the sensor may be heated. Active heating of the sensor allows for operation of the cartridge in environments cooler than 10 to 15 Celsius.

The housing preferably comprises a series of baffles to remove saliva aerosol from a vapour sample, so that substantially only vapour reaches the cartridge. Alternatively or additionally, one or more baffles is optionally provided in the cartridge. Yet further alternatively, a single baffle may be provided in each of the housing and the cartridge.

The housing preferably comprises a valve system to provide at least two flow paths through the complex device. Thus, an exhalation breath may be directed through a first flow path and an inhalation breath may be directed through a second flow path.

The housing and/or the cartridge, and preferably the cartridge, further preferably comprises a flow rate sensor for measuring breath flow rate.

The housing and/or the cartridge, and preferably the cartridge, further preferably comprises a carbon dioxide sensor for measuring a carbon dioxide concentration in breath.

The housing and/or the cartridge, and preferably the cartridge, further preferably comprises one or more humidity sensors. There may be more than one humidity sensor, for sensing the humidity of breath or ambient air, for example.

The housing and/or the cartridge, and preferably the cartridge, further preferably comprises a temperature sensor for measuring breath temperature.

The housing and/or the cartridge, and preferably the cartridge, further preferably comprises a pressure sensor for measuring breath pressure during exhalation or inhalation.

Thus, the housing and/or cartridge optionally measures physical and chemical parameters on the patient's breath including: rate of breath exhalation, the water content of the breath exhalation, the temperature of the exhaled breath, carbon dioxide levels on the exhaled breath, breath pressure etc.

The analyser is able to monitor these various sensors and use them about to give feedback to the user in real-time, so that the user can modulate their breathing profile. This feedback can be given in several forms including visual or audio.

The housing conveniently further comprises an electronic interface for providing information from one or more sensors to an external device and/or for receiving electrical energy from an external source. The electronic interface may provide information in an analogue or digital form.

The housing preferably further comprises a data processing unit. The data processing unit may comprise an analogue to digital converter. The housing may further comprise a transmittal means to transmit information or data to an external device. Additionally, a data storage means can be included. The housing may comprise an electronic interface for a removable data storage means.

The housing preferably further comprises an audio output to provide a user with feedback and/or instructions to assist the user with keeping breath parameters (such as pressure or flow rate or the like) within a desired range.

The housing preferably further comprises a display. The display may provide a user with information about a breathing cycle in real time or in near real time. The display may provide a user with feedback and/or instructions to assist the user with keeping breath parameters (such as pressure or flow rate or the like) within a desired range.

Preferably, the condensation zone has a lid which at least partially covers said condensation zone. This configuration is particularly advantageous because a partial lid aids the retention of the condensate within the analyser and channels the breath condensate towards the channels and the sensing zones.

Preferably, the analyser includes analysis initiation means to detect the presence of a condensate.

This configuration is particularly advantageous because it enables the functions for analysis of a breath condensate to be carried out in a single integrated device which decreases any delay and likelihood of error associated with movement of condensate samples. A further level of control of the system is therefore provided to produce analysis without need for an operator involvement.

Preferably, the or each discrete region has a specified volume, which allows the measurements to be calculated based upon the volumes.

The specified volume may be up to approximately 4 μl.

Preferably, one or more discrete regions has a specified volume such that there is an analyte detection zone whose volume is less than the volume of condensate from one exhaled breath. This allows for the measurement of a determined volume of the breath condensate.

Preferably, a surface of a discrete region includes a surface coating, said coating including reagents to engage the condensate and determine composition.

This configuration is particularly advantageous because it means there is no necessity for a liquid reagent to be added to the sample thus minimising dilution errors and providing a device which has both an extended shelf life and is easier to manufacture.

Preferably, the surface coating has a thickness in a range of between 1 μm to 15 μm.

Preferably, a discrete region includes a pair of electrodes in operable connection with a condensation zone, the electrodes being maintained at different potentials. Further preferably, the potential between the pair of electrodes is variable. The use of electrodes allows accurate determination of the analyte and moreover provides a long-lasting means of analysis, allowing a device to be stored for extended periods without degradation of accuracy.

Optionally, a reagent is added to said condensate in a further discrete preparation region.

This allows the use of chemicals and reagents that would be intrinsically incompatible if formulated together, or stored in intimate contact to be prepared within the device, except with adequate physical separation to prevent interaction, reaction and or degradation during manufacturing and storage.

Preferably, one or more regions are temperature controlled.

This configuration is particularly advantageous because the different functions of the analyser require different temperatures at which to work best, therefore zones can be held at the same temperature or different temperatures and the temperatures can be changed during the operation of the device and the temperature within a zone can be controlled relative to ambient temperature.

Preferably, the reagents for the analysis of the condensate are loaded into the condensate sample during passage of the condensate sample from the condensation zone to a detection zone. This assists in the detection and analysis of analytes within the condensate.

Preferably, a discrete region has a perimeter ranging from 2-10 mm, and especially a perimeter of 5 mm.

Preferably a discrete region has a height of approximately between 75-750 μm, and especially a height of 100 μm.

A discrete region may comprise a chamber, the chamber being enclosed on five sides with a sixth side open for fluid to enter the said chamber and for displaced air to escape therefrom.

It is preferred that the condensate forms a film rather than droplets. The described features of the region aid the formation of a film. Films have a controlled flow and eliminate the occurrence of air trapped within the chamber. Optionally, this is achieved through the selection of a surface material for the condensation zone having an appropriate contact angle with the breath condensate, and preferably around 20°.

Preferably, multiple breath condensates may be collected and analysed simultaneously, to provide a more efficient device.

Optionally, the device includes transmission means such as a cable, Wi-Fi connection to enable information on the analysis to be transmitted to processing and display, allowing a user to review the results. Interventions from the operator are further minimised therefore removing one of the biggest sources of inaccuracy due to user error when performing manual tasks.

Preferably, any interference to the determined values are measured and accounted for in the final signal.

This configuration is particularly advantageous because it allows the signal to be calibrated to produce an accurate result and with a reduced number of errors.

Conveniently, the power to the condensation zone is determined enabling calculation of the flow rate of exhaled breath, or rate of exhaled breath condensation and the total volume of exhaled breath collected. This has a number of advantages as the efficiency of the device can be determined to ensure it remains within acceptable parameters. Also, the volume can be used to determine the breathing efficiency of the user.

Preferably, the analyser further comprises a hole or channel through which air can escape from the cartridge device, said hole or channel connecting a discrete region with atmosphere, so allowing air to leave the device and preventing air from getting trapped within the device as the breath condensate flows in.

The cartridge may be shielded from direct contact with ambient air, to avoid so far as possible, contamination from condensation from ambient air.

The cartridge may be shielded from ambient light, to avoid so far as possible breakdown of any photoactive species which may be present in a breath sample.

The cartridge device may be adapted so that when the cartridge device has determined that sufficient condensate has been collected it is able to electrically activate the cartridge and make measurements upon the exhaled breath condensate, thus determining the concentration of analytes within the exhaled breath condensate.

Optionally, the assay is automatically started when a cartridge filled condition is met, such as the electrical shorting of two electrodes by the liquid sample.

The analytes are optionally converted by an enzymatic reaction into an electrochemically active molecule, which is detected by electrochemical analysis. The enzyme formulation is a soluble formulation which dissolves into the condensate sample and the reaction proceeds in the homogenous phase. An electrochemical reaction starts on the application of a voltage, the subsequent current is proportional to the analyte of interest.

Electrical connection of a cartridge to a housing is made through a plurality of contacts assigned either to the assay detection, temperature monitoring, temperature control, automatic assay starts or electrochemical detection.

The device is shielded from the ambient atmosphere to minimize the co-condensation of ambient humidity that would otherwise confound the analysis.

The device has a unique identifier on it which holds information regarding details of calibration and when the device was made. This data can be read by the reader device and used to improve the accuracy of the overall device.

Near the completion of filling a chamber the breath film condensate dissolves patches of salt, the salt is necessary for both fixing the potential at a silver/silver chloride reference electrode and for providing a relatively low impedance sample.

This design means there is no manual handling of the sample, the sample is protected from accidental contamination there are moving parts are required to move the sample, and the sample can be guided into a chamber without entrapping air. Once condensed the sample is in contact with the cartridge through the transportation and analysis.

Optionally, addition of reagents to a condensate is achieved through a penultimate dissolution of chemicals into the breath condensate during the passage of the sample over a surface, or the absorption of the sample into functionalized films.

Exhaled breath is condensed on a functionalised surface, whose functionalisation is optimised to maximize the efficiency of condensation of a breath film, the surface has been systematically optimised and characterised to minimise droplet formation and instead form a film across the surface. Unlike previous devices in which a microfluidic chamber is incorporated the final analysis chamber with no air vent for the expulsion of trapped air, instead in the present concept air leaves by the same route as the liquid enters. The liquid is initially guided to the bottom of the chamber, so the chamber is bottom up filled thus air bubbles are not trapped.

The device is laid out so that multiple chemical and biochemical steps can be carried out on the condensate either in parallel or sequentially.

Distinct patches of reagents are laid out within the device, including: buffers, salts and enzymes.

The breath film condensate is guided into the fixed volume sensing chambers. As the solution enters the chamber it sequentially reaches enzymes and the salts. The dissolution of both patches can be distinct or overlapping with respect to time.

The specific analytes of interest for measurement can be detected in the final sensing chamber by the use of molecules, macromolecules, ions etc. including but not exclusively: antigens, antibodies, RNA, DNA, proteins, enzymes, ionophores etc. These biochemical reactions are designed to give a signal that is proportional to the analyte of interest.

The inventive device for collecting exhaled breath condensate and for determining substances within the condensate includes at least one condensing zone and at least one sensing zone. The zones are joined in such a way at to expedite the transfer of condensate to the sensing zone whilst undergoing any necessary purification or sample enhancement. There is a tapering fluidic lay-out so the film is collected in a large area which narrows down to a smaller and smaller area hence concentrating the film onto a final sensing zone.

After a short period of time, and upon adequate sample reaching the sensing zone an assay or measurement can take place upon the sample. The initiation of the assay can be automated by a start condition which can be an electrical signal produced by applying a voltage between two electrodes.

In a further embodiment the temperature of the condensing zone can be set relative to the ambient temperature and the power necessary to maintain the temperature is both indicative of the rate of exhaled breath and the power necessary in the change of phase from the gas, vapor and aerosol phase to the liquid condensate phase. Many biochemical, molecular biology and chemical reactions are temperature sensitive and so the reaction zone has an integrated heater preferably on the back side for elevating the temperature above the ambient temperature and above the condensing zone temperature.

Active heating of the temperature zone allows the assays to be run in cold environments such as horse stables where the temperatures can be below 10 to 15 Celsius.

The analyser has been carefully engineered to deliver an analyser whose operation requires minimum interventions from the operator, therefore removing one of the biggest sources of inaccuracy due to user error when performing manual tasks. In addition, the analyser has been designed with no moving parts. Instead a combination of good design and materials science is used to cool, guide and prepare the sample, with no complex pumping strategies. The breath condensate film is guided by a fluidic layout which tapers into a final chamber. The driving force for flow of the breath condensate film is provided by a combination of gravity, capillary and tapering channels. In addition, the analyser can introduce multiple reagents into the sample, all of which are deposited and or packed and stored upon the device in a dry manner thus optimizing shelf life stability. The entire analyser including the cartridge device is integrated so the sample never leaves the device from condensation to final detection, therefore eliminating the risk of sample contamination or sample loss. Similarly, concerns regarding cross-contamination between samples are eliminated as all the wetted parts can be disposed of after each assay.

The analyser optionally includes a mouth-piece, the mouth-piece comprising an entry port and an exit valve, and interposed therebetween a plurality of chambers to direct fluid flow from the entry port to the exit valve, the chambers being so configured to cause a change of 90° in the direction of fluid flow. Further optionally, at least two chambers are separated by a one-way valve.

In operation the cartridge device is shielded from the ambient humidity behind walls and valves, this reduces the co-condensation of ambient humidity which would otherwise dilute and contaminate the breath condensate film.

Also disclosed is a mouth-piece comprising a mouth-piece body, having an entry port and an exit valve, and interposed therebetween a plurality of chambers to direct fluid flow from the entry port to the exit valve, the chambers being so configured to cause a change of 90° in the direction of fluid flow. Optionally, at least two chambers are separated by a one-way valve.

The signal gathered directly from the analyte or measurement of interest can be calibrated relative to a number of other signals, including: sensing zone temperature, sample conductivity, ambient temperature, breath flow profile, breath condensation profile, breath carbon dioxide profile.

With many sensing based systems the magnitude of the final signal and the sensitivity of the signal to the analyte or measurement of interest can be a variable between sensors from the same manufactured batch and for sensors from different manufactured batches. In the current system the errors caused by sensor variability within batches and between batches are removed both through device characterization at the point of use and also by calibration factors determined during the device's manufacturing. Lastly any changes in the sensitivity of the devices due to aging can be calibrated for by a calibration factor whose input is the age of the device.

BRIEF DESCRIPTION OF THE DRAWINGS

The invention is now described with respect to the accompanying drawings which show, by way of example only, embodiments of a breath-condensate collector and analysing device.

In the drawings:

FIGS. 12a-12f illustrate a valve system to prevent entry of the ambient air into a condensed sample.

DETAILED DESCRIPTION OF THE INVENTION

Figure 1:
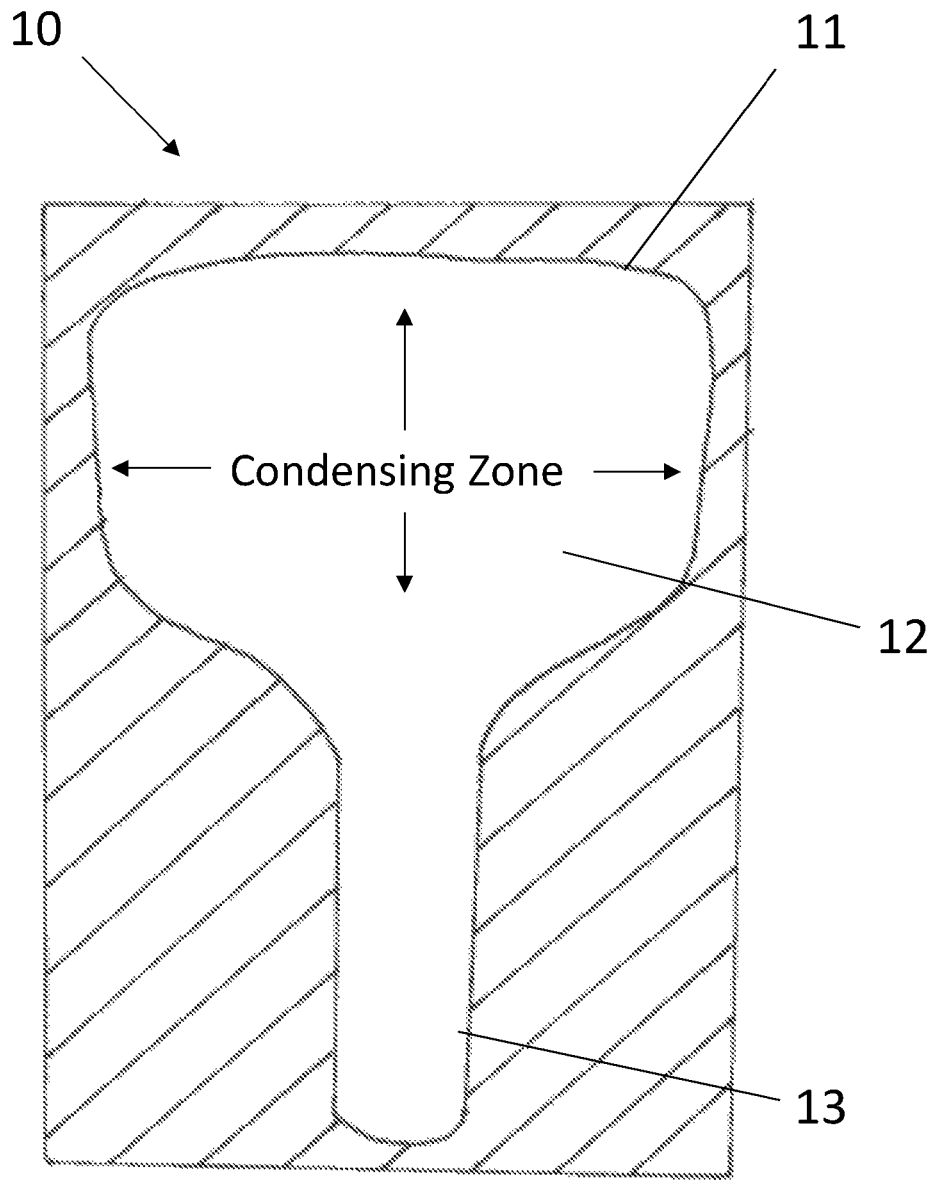
FIG. 1 illustrates the layout of a device.

The analysis of exhaled breath to determine physiological dysfunction in a person or animal has been known for many years. The presence or otherwise of components of the breath can show deficiencies in the body, such as lung function or cell function. To this end, devices have been developed, which aim to collect the exhaled breath, including the more volatile components, which are otherwise not captured and so escape analysis. In many devices, the breath is first condensed to liquid or solid form, which is then analysed.

There are however problems which need to be overcome in obtaining an analytical result. Many devices leave the user with the problem of carrying out the analysis. Often the condensed sample needs to be transported to a location remote from that where the analysis was carried out. However, some of the breath components which need to be characterised, such as hydrogen peroxide, are inherently unstable and so will have decomposed to an extent before any analysis is carried out. Although steps can be taken to alleviate this problem, such as cooling the sample in transit and also extrapolating back, based on the time since the sample was taken, to an estimated value, these steps can be difficult to carry out and increase the error limits for any particular result.

Carrying out an analysis in situ, directly the sample is taken, overcomes the above to a large extent, but brings with it the problems of analysis as, especially where an animal is concerned, this may be at a distance from any building. Also, there will be a need for the analyst to have calibrated reagents to hand.

The present invention seeks to alleviate the above disadvantages by providing a hand-held device, which both collects and analyses exhaled breath.

To achieve this, in a broad aspect, the invention provides an analyser, ideally hand-held which allows a user to breathe into the analyser, the breath being separated firstly in a mouth-piece, into component parts to direct alveolar air from the lungs onto a cartridge device held in an analyser housing. The cartridge device has a condensation zone, or collector, to condense breath impacting the condensation zone and then transporting a sample of the condensate to an analyser, fluidly connected to the condensation zone where analysis is carried out using a solid-state analytical element. The use of a solid-state element removes the need for calibration of liquid reagents and removes the risk of dilution errors. Such an analyser also provides a longer shelf life than conventional devices and is more easily manufactured. To reduce the number of moving parts within the analyser and so increase reliability, the condensate preferably moves through the cartridge device by capillary action, and also optionally using functionalised surfaces to increase flow between regions. Ideally, between condensation of the sample and analysis should be no more than 30 seconds. In one embodiment the analyser includes a housing to receive a replacable mouth-piece and cartridge device.

In more detail, the user breathes into a mouth-piece, typically incorporating baffles to aid separation of breath constituents, the breath exits the mouth-piece and the exhaled breath is condensed on a surface, optionally functionalised such that any functionalisation is optimised to maximise the efficiency of condensation and to maximise the flow under gravity or otherwise of condensate phase from the condensing zone to integrated fluidic channel provided. The cartridge device is laid out such that multiple chemical and biochemical steps can be carried out on the condensate either in parallel or sequentially. The channel layout provided, means that where chemicals and reagents are utilised during the analysis, these can be sequentially added to a sample as the sample flows over the series of chemical and reagent zones provided therefor. This arrangement allows unstable reagents, including those which are unstable in the presence of other reagents, to be prepared or stored in close proximity to one another, yet spatially separated to prevent interaction. Reagents and sample conditioning additives are able to be added at several different points within the device.

Finally, the condensate enters one or more sensing chambers, each having a fixed volume. Any remaining reagents, which can include proteins, enzymes, macromolecules, surfactants, ions etc. necessary for the analysis can be present here as dry mobile or immobilised formulations in close or intermediate proximity to the final point of analysis. The specific analytes of interest can be detected in the final sensing chamber by the use of such reagents, which can further include antigens, antibodies, RNA, DNA, proteins, enzymes, etc. Analytes to be detected include, but are not limited to: glucose, lactate, ketones, hydrogen peroxide and nitric oxide and may be detected either directly or indirectly.

Detection is preferably carried out electrochemically to increase the accuracy and reproducibility of results. In one embodiment, two parallel electrodes are provided, which when not in use are electrically isolated from each other. In the presence of a liquid between the electrodes, a soft short is caused which produces a measurable electric signal, which can be used to determine the level of analyte. Such a signal can also be used to determine the arrival of condensate into the cartridge and so initiate further analytical steps.

The reagents used are designed to give a signal that has a known relationship, such as being proportional, to the concentration of the analyte of interest. The reagents may be present in a form such as dried down in place, a lyophilized bead or a film or any other suitable form. The advantage of using a dried reagent is that such reagents tend to be more storage stable and their concentration is likely to be more accurately known. The reagent may be a film such as a polymer blend containing a biologically compatible polymer, a macro-biological molecule or a mediator. In addition, other reagents such as a biologically-compatible polymer, for example polyurethane, horse-radish peroxidase or a surfactant such as sodium dodecylsulphate can also be present. As examples of mediators, then for hydrogen peroxide analysis in particular, potassium ferrocyanide and/or ferricyanide can be used.

Figure 6:
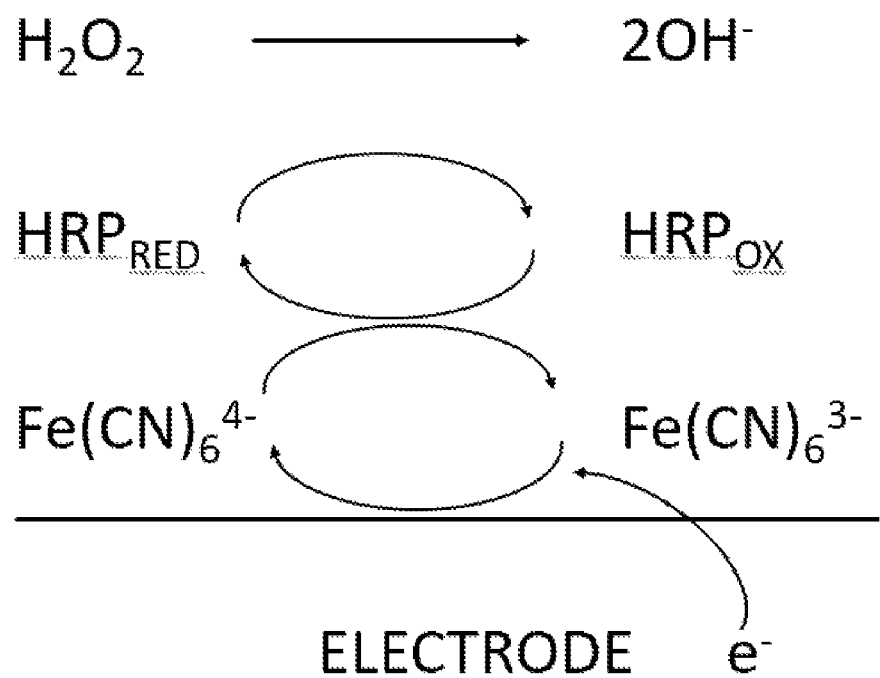
FIG. 6 illustrates an example of chemical reactions involved within the sensing chamber

As an example, illustrated in FIG. 6, hydrogen peroxide can be detected indirectly with the use of horse-radish peroxidase (HRP). The reduced form of HRP initially reacts with the hydrogen peroxide to produce an oxidised form. The oxidised form subsequently reacts with potassium hexacyanoferrate (II) (potassium ferrocyanide) to produce potassium hexacyanoferrate (III) (potassium ferricyanide). Potassium ferricyanide is then detected by use of an electrochemical method such as amperometry where the current flows from an electrode. The current flowing is proportional to the concentration of the produced potassium ferricyanide and the final current is therefore indirectly linked to the initial hydrogen peroxide concentration in the sample. In detecting the ferricyanide species, this is reduced back to the ferrocyanide.

The temperature of the condensing zone can be set relative to ambient temperature. The power necessary to maintain the temperature difference can be utilised to determine the rate of generation of exhaled breath. To achieve this, the power necessary to maintain the temperature is monitored. As this is a function of the thermal energy generated by the change of phase of the exhaled breath to the liquid condensate phase, measurement of the energy can be converted into a volume of condensate produced.

In a preferred embodiment, a Peltier device may be used to cool the condensing zone. The temperature on the face of the cooling zone itself may be static or dynamic. In a preferred embodiment the temperature would be around 10° C. although it should be appreciated that the temperature may change depending on the various parameters including ambient conditions. Should atmospheric air be excluded as in certain optional embodiments of the device then a lower temperature of around 5° C. can be used.

The integrated nature of the analyser produced allows for the provision of an analyser whose operations require minimum interventions from an operator which removes a source of inaccuracy from the results. In addition, the lack of moving parts in preparation and analysis of the sample again improves the results obtained and also imparts a longer lifetime to the device. Further, the analyser can introduce multiple reagents into a sample, all of which reagents are stored within the cartridge device in a dry manner, which improves the shelf life of the reagents. Finally, the sample under analysis does not leave the analyser between the time of condensation and final detection, which minimises the risk of contamination or loss of sample. Furthermore, as elements used as part of the analysis can be disposed of following use, which again reduces the risk of cross-contamination. Yet further the analytical elements of the analyser can be incorporated into a removable section, such as a cartridge device, which allows, once the other elements of the analyser have been cleaned or otherwise readied for use, a new cartridge to be inserted ready for further use. Separate measurements on different subjects can thereby be rapidly made, and analysis on a subject be made, whilst the results are being obtained from a previous subject. Alternatively, measurements of different exhalates made for the same subject relatively close to each other in time.

It is anticipated that the usable liquid volume within a cartridge is from 5-40 µl and preferably 10-30 µl.

On analysis, the signal generated from the analyte or measurement of interest can be calibrated relative to a number of other signals, including the sensing zone temperature, sample conductivity, ambient temperature, etc. Again, therefore the errors caused by sensor variability within batches and between batches is removed both through the analyser characterisation at the point of use and also by factors determined during the analyser's manufacturing.

In order to remove variations in analytical results carried out using electrodes, due to different concentrations of chloride ion in a sample, then a standard electrode concentration of chloride, typically a saturated solution, can be formed of the sample. This can be achieved through the condensate passing over a surface onto or within which a chloride, such as sodium chloride, has been added. This can be for example within a gel layer, from which chloride ions can readily diffuse out. Signals obtained from an electrode can therefore be attributed to an analyte of interest as the electrode response due to the salt can be filtered out.

Signals from the analysis and also from the power usage of the cooling applied to the condensing zone can be fed to a processor, either attached to the analyser or externally, which then generates the data required by the user. Additionally, by performance of a mass-balance calculation on the condensate collected and the condensate entering the sensing chamber, the analyser can calculate the distribution of sample throughout the analyser and determine whether a cartridge has leaked or blocked, which allows quality checks to be built into the analyser.

Referring now to FIG. 1, this illustrates a first embodiment of an integrated collection and analysis cartridge device, or device, for use as part of an analyser. The device, generally referenced 10, is operatively linked to a mouthpiece (not shown here) through which exhaled breath is directed onto a breath collection portion 11 having a condensing zone 12. The condensing zone 12 is in fluid connection with the sensing zone 13 in which analysis of the collected condensed breath fluid can take place. It will be appreciated that when the device 10 is in fact held such that the condensing zone 12 is uppermost, then flow of fluid into the sensing zone 13 is facilitated by gravity. Although not illustrated in FIG. 1, the condensing zone 12 and sensing zone 13 are fluidly connected by one or more channels, to provide a controlled flow of fluid. The dimensions of a channel are of an order of magnitude less than those of the overall device 10 although the dimensions of a channel may vary depending on the function of the channel. Moreover, the dimensions of a channel can vary along the length of the channel. In a further non-illustrated embodiment, flow of the fluid from the condensing zone to the sensing zone is controlled by means of firstly collecting and holding the condensed fluid in one region and subsequently causing a portion of the collected fluid to flow into the sensing zone in defined aliquots.

Figure 4:
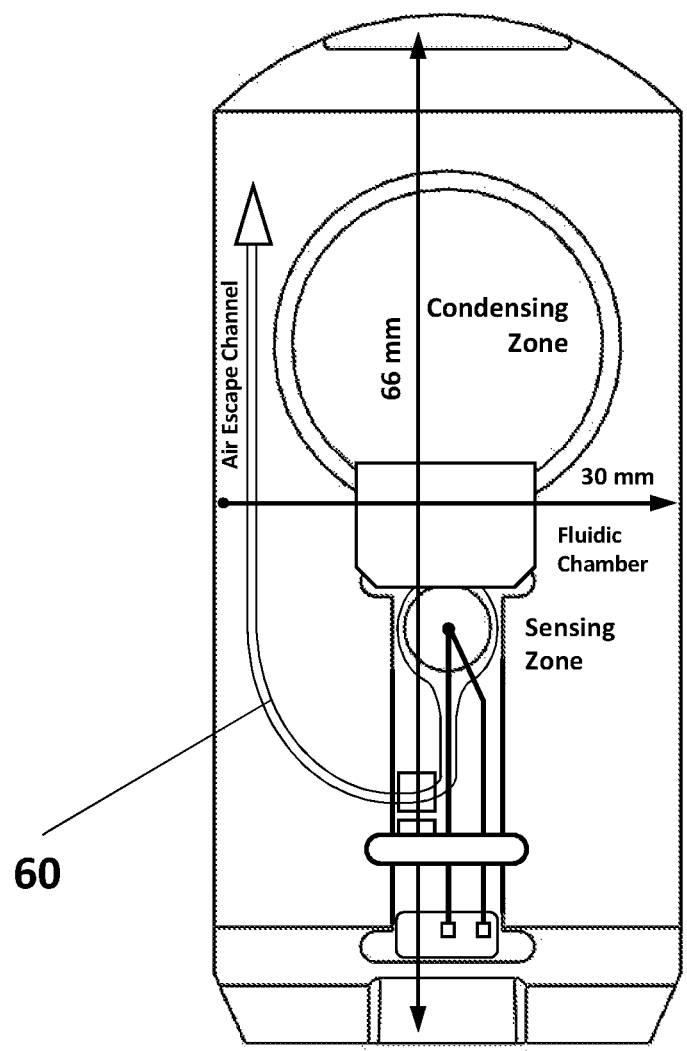
FIG. 4 illustrates the layout of an embodiment of the device.
Figure 5:
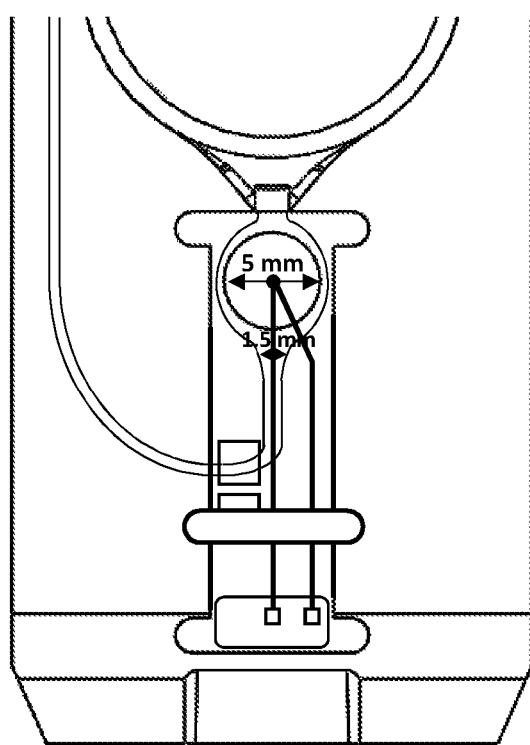
FIG. 5 illustrates a close-up view of the layout of the sensing zone of the device.

In a preferred embodiment the overall dimensions of the device 10 are 66 mm×30 mm×5 mm, as illustrated in FIGS. 4 and 5. The condensing zone 12 and the sensing zone 13 are each approximately circular in the preferred embodiment, although they can have a polygonal shape. The size can be varied to suit the use. The condensing zone 12 preferably is of larger dimension of the order of that of the entire device 10. The sensing zone 13 can have a perimeter of approximately between 2-10 mm and of approximately 5 mm. The height can be approximately between 75-750 µm and especially of 100 µm.

Figure 1A:
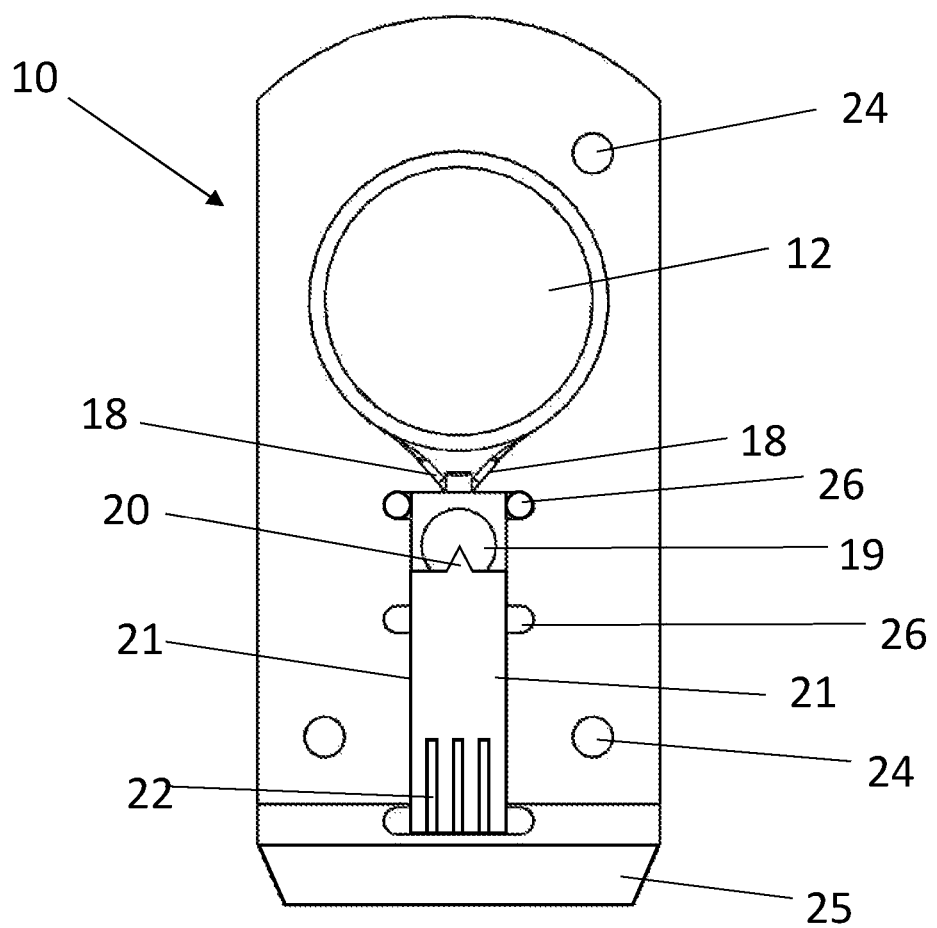
FIG. 1a further illustrates layout of a device.
Figure 1B:
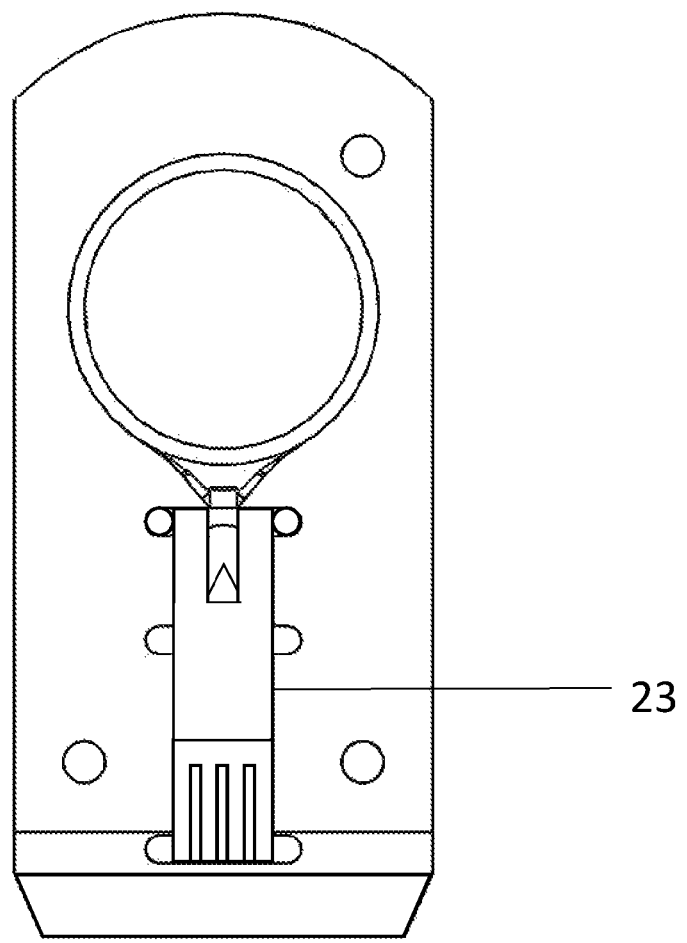
FIG. 1b is a further illustrative layout of a device.

FIG. 1*a* illustrates features of the device 10 in more detail. Breath is condensed on the condensing zone 12 and forms a film on the surface thereof. The condensed fluid exits the condensing zone 12 by capillary action, via the channels 18, which lead the fluid to the sensor element 19. The sensor element 19 as shown is a combined counter and reference electrode, although in a separate embodiment, these can be located separately. The working electrode 20 is housed as part of a ceramic sensor 21. Electrical contact pads 22 at the distal end of the ceramic sensor 21 enable electrical connection with corresponding elements on the apparatus housing into which the device 10 fits when in use. A cover 23 is provided (FIG. 1*b*) which then defines a microfluidic chamber beneath the cover 23.

In order to aid correct alignment of the device 10 within a housing, key holes 24 are provided engaging corresponding projections in the housing. Additionally, to aid insertion of the device 10 into the housing the distal end 25 of the device 10 has a wedge shape. The sensor element 19, ceramic sensor 21 and cover 23 are held in position relative to the device body 10*a* by an epoxy resin fixing 26, although other fixing means, including mechanical, can also be utilised.

In a further preferred embodiment, the or each channel (not illustrated) has a means of allowing air to leave the device 10, for example when the sample flows into a channel. An example of the means may be a further channel or an aperture through which the air can escape. This prevents air from getting trapped within the device 10 as the fluid flows in as the air has a route by which it may leave. An example of this embodiment is shown in FIG. 4 and in FIG. 5.

In an alternative embodiment, the device may include an air escape channel 60 as illustrated in FIG. 4.

In order to condense the exhaled breath, which comprises a mixture of gases and vapours, into one volume the condensing zone 12 is provided with cooling means. The constituent elements of the sensing zone 13 can also be provided with cooling or heating means, where required, to assist in the analysis of the breath condensate. For example, where an assay incorporates an enzymatically catalysed reaction, it is usually advantageous to carry out the reaction at around normal body temperature. An example of a heater which can be used to elevate the temperature of a reaction is a conductive strip, which can be screen-printed and secured to the back of a sensor adjacent a sensing zone. On passing a current through the strip, using for example Ohmic heating, the temperature can be controlled using a pulsed voltage across the heater.

Additionally, or alternatively, a thermocouple sensor can also be included, preferably printed onto the sensor to achieve intimate contact with the sensor and give an accurate value for the sensor temperature. An external temperature sensor can however also be used.

To facilitate collection of condensate in one region of the condensing zone 12, the condensing zone 12 can have a coated surface to direct condensed breath optionally towards a particular region of the condensing zone 12 which particular region can be maintained at a lower temperature than other regions of the condensing zone 12. The surface coating is preferably of a hydrophobic nature, but can also be or hydrophilic where suitable. Additionally, a coating can be provided which is both hydrophobic and lipophobic so that both oils and water run readily off the surface. Such coatings can be those known in the art such as perfluorinated polymers, for example that marketed under the trade name Teflon®. When dried, the thickness of the coating can be in the range from 1 µm to 15 µm. The coating may swell to a greater thickness when it comes into contact with the sample.

Figure 7:
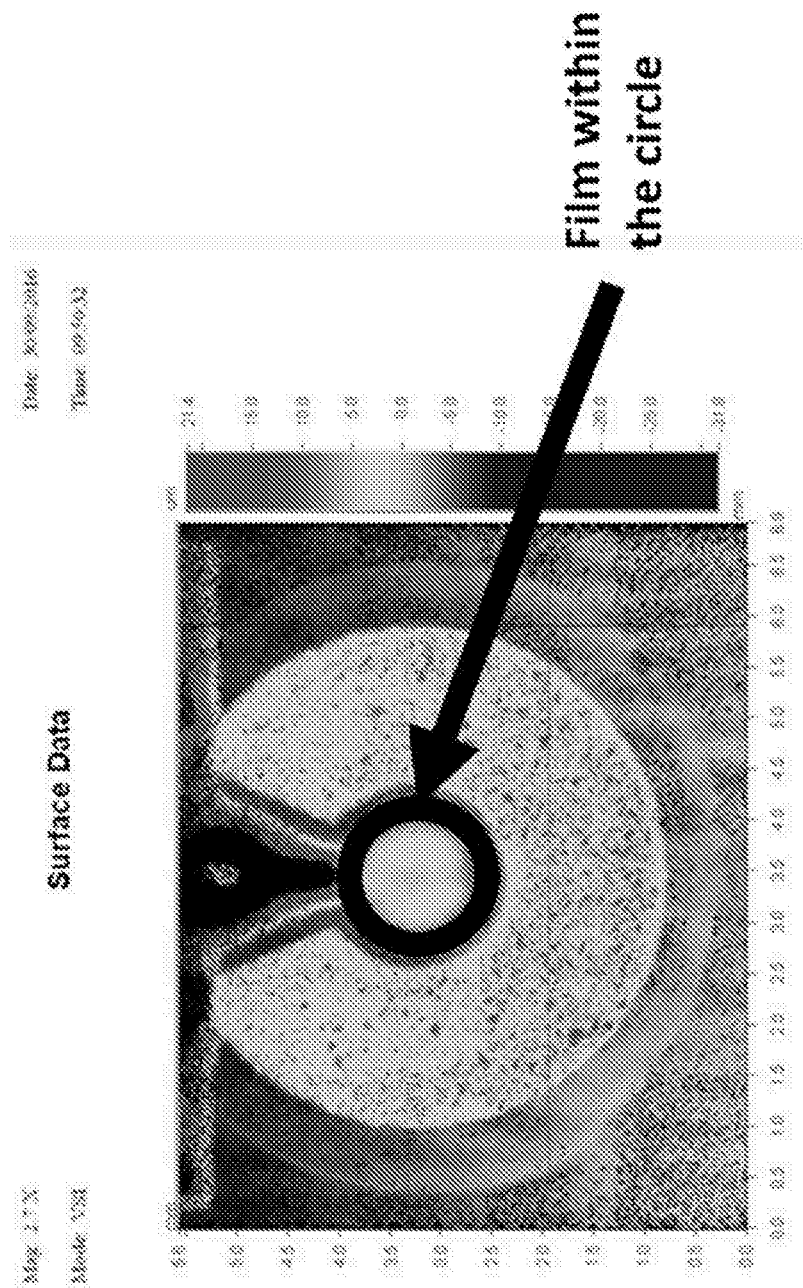
FIG. 7 illustrates an example of an embodiment of a film coating.

FIG. 7 shows an example of a coating by a film of a circular area. In this embodiment, the circular area covered by the film coating has a height of 5 µm.

Figure 2:
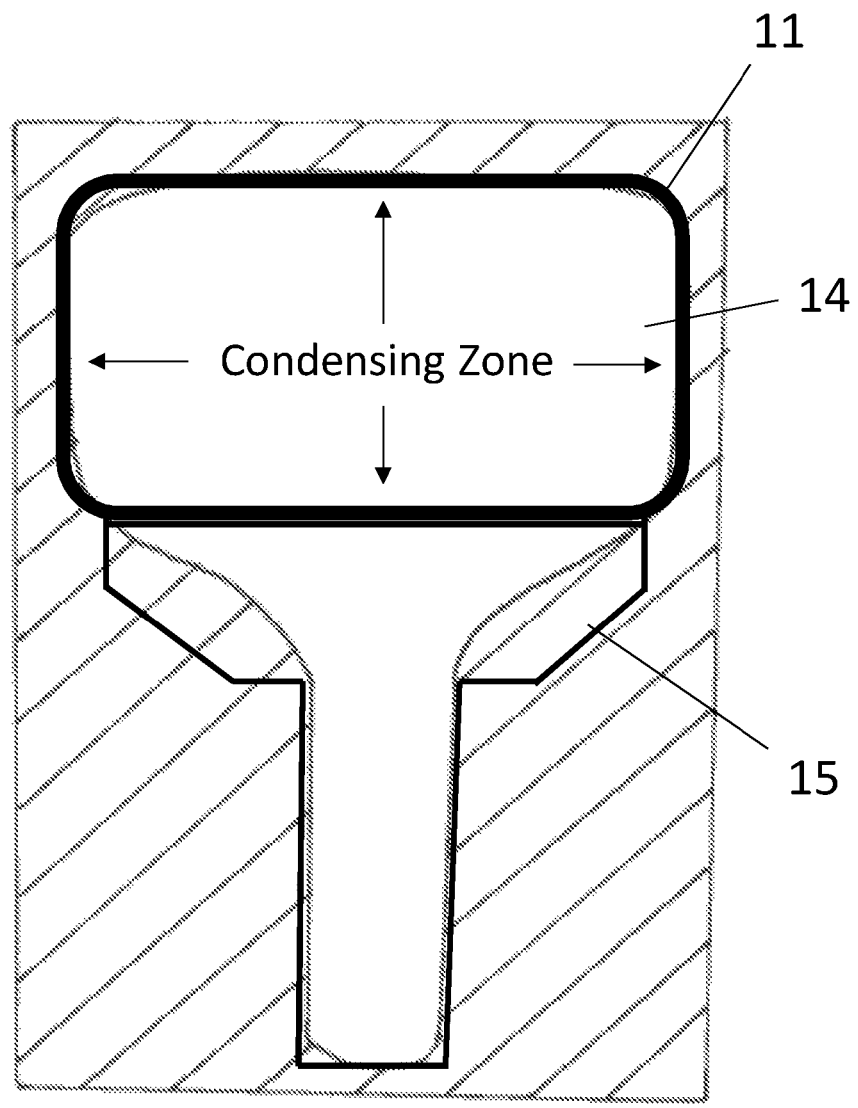
FIG. 2 illustrates a second embodiment of the device, including lids to retain sample and guide flow within the device.

One or both of the condensing zone 12 or sensing zone 13 (see FIG. 2) can be at least partially covered by a lid 14 or 15 respectively. In FIG. 2, a lid 14 is shown, located around the perimeter of the condensing zone 12, which lid 14 acts to retain condensate within the condensing zone 12. The lid 14, which partially covers the condensing zone 12, also acts to minimise outflow of breath from the collection portion 11, and restricts loss of breath which does not immediately condense on contact with the condensing zone 12. The open area between the perimeter regions allows the exhaled breath to reach the surface of the condensing zone 12.

The lid 15, located over the sensing chambers of the sensing zone 13 and the channels, allows the volume to be controlled, and the sample to be retained, whilst also promoting wicking of the sample into and along a channel or channels. The volume of the sample is kept small through use of the lid to aid analysis, the lid also eliminating turbulent flow and mixing.

Figure 3:
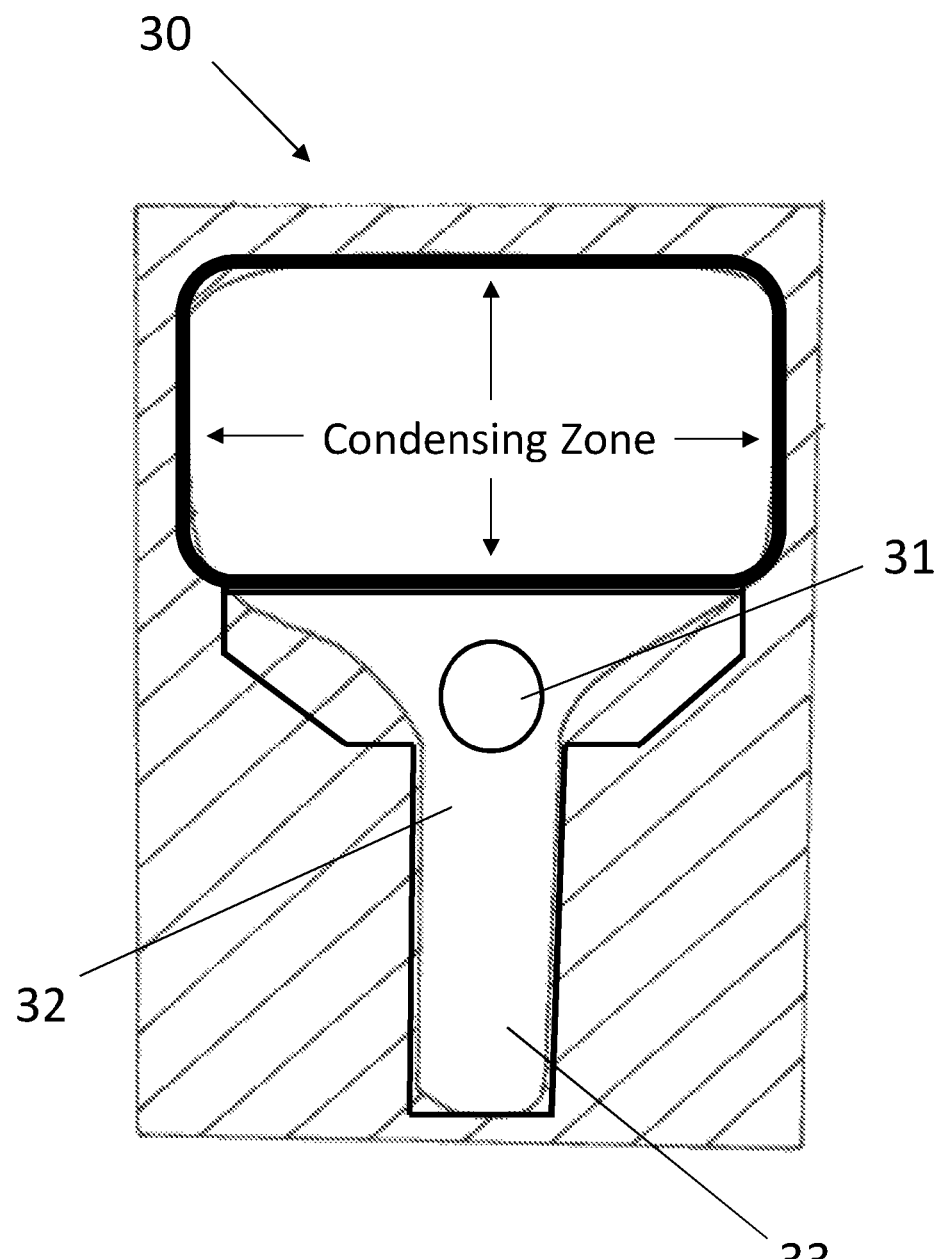
FIG. 3 illustrates further features of a device.

FIG. 3 illustrates a cartridge device 30, having a further sample preparation zone 31, in which initial reagents or other modifiers can be added to the sample to facilitate the analysis in the sensing zone 32. The purity of the sample can also be determined prior to the sample passing through the sensing zone 32 and into the analysis region 33.

The sensing chambers optionally are operatively connected to a sample sensor which determines whether a sample is present. Additionally, the level of sample within a sensing chamber can also be determined. Once a pre-set level is reached, the level sensor transmits a signal so that assay commences automatically without input from the operator. This reduces the time at which analysis begins.

Figure 8:
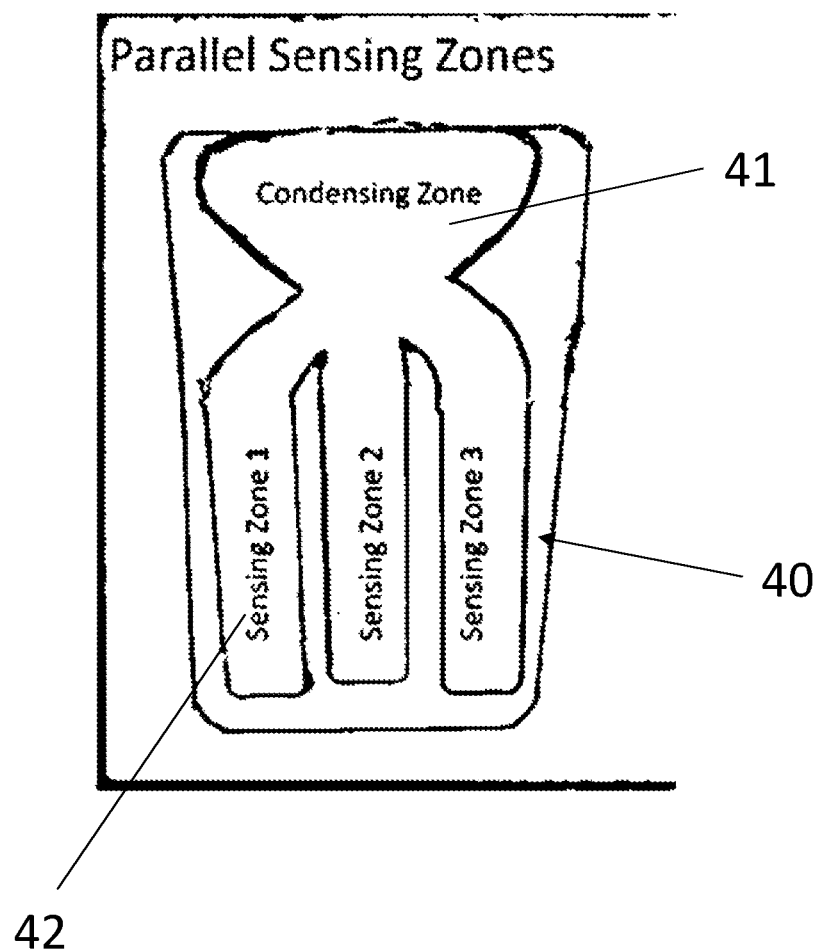
FIG. 8 illustrates an alternative layout of the device.
Figure 9:
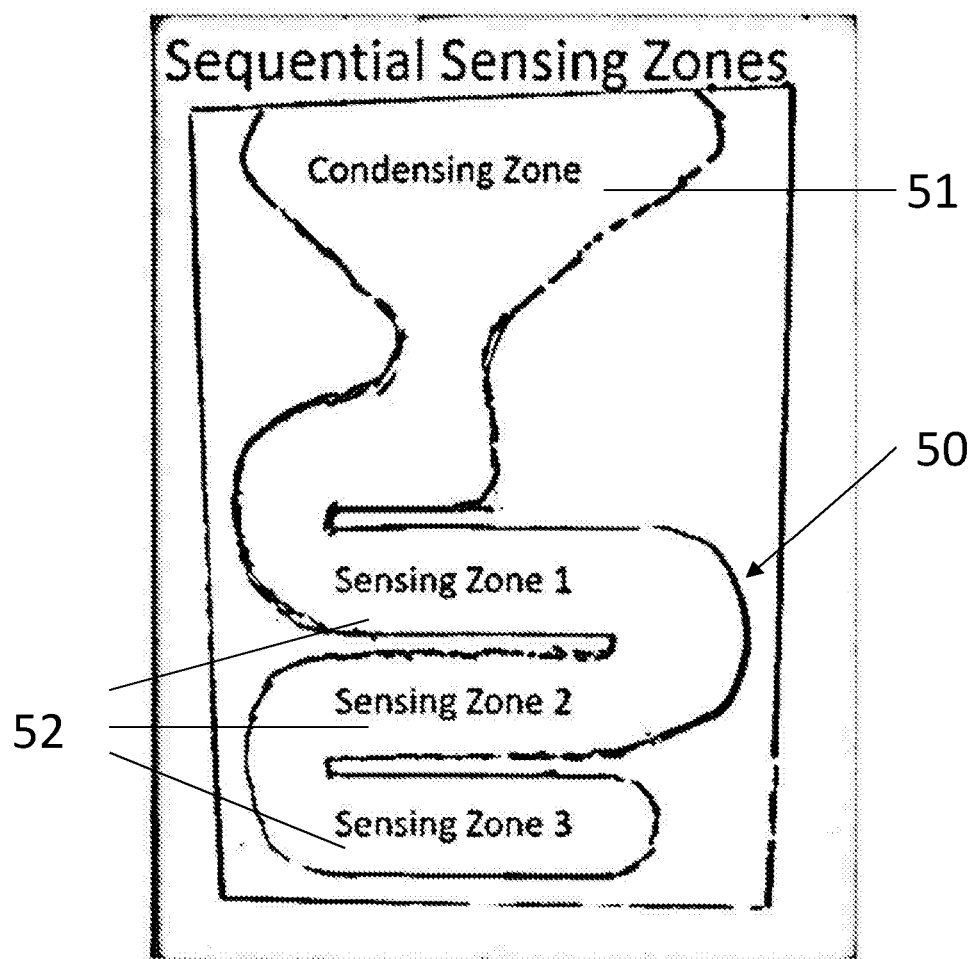
FIG. 9 illustrates an alternative layout of the device.

FIGS. 8 and 9 show alternative embodiments whereby the sensing zones 42, 52 may be laid out within the device 40, 50 either parallel to one another below the condensing zone 41, 51 (FIG. 8) or sequentially (FIG. 9).

Figure 10:
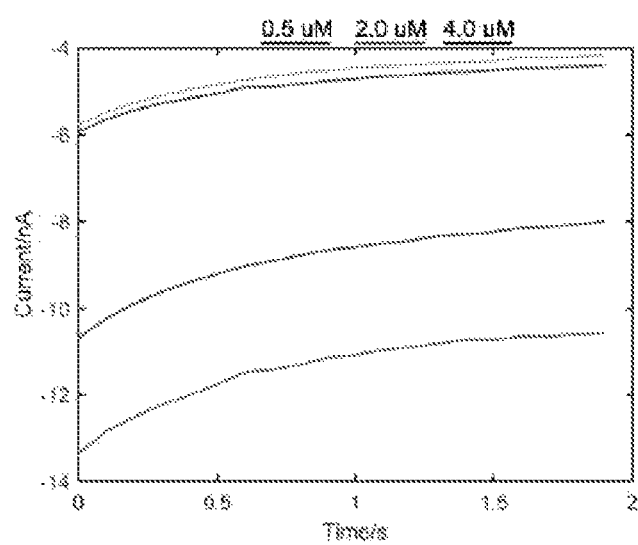
FIG. 10 is a chart showing raw noise data.
Figure 11:
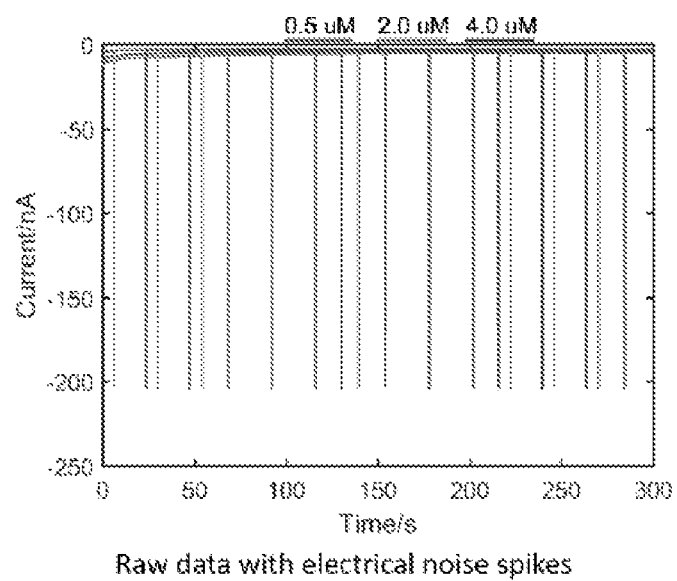
FIG. 11 is a chart showing electrical noise spikes.

FIGS. 10 and 11 shows how interference from various sources both known and unknown, can distort the signal produced. In the preferred embodiment, the spikes within the raw signal will first be identified by the reader and contribution of the spikes will be removed from the raw signal before the analyte concentration is calculated.

In an alternative embodiment of a device, not illustrated, the device includes control means to govern the passage of condensed fluid from the condensing zone to the sensing zone. This allows the condensed breath to be moved for analysis in a known, controlled manner.

As an example, the breath can be collected with the device so oriented that the condensation zone and particularly the fluid connection between the condensation zone and the sensing zone is a non-vertical, perhaps horizontal orientation, so that fluid flows relatively slowly or perhaps unevenly therefrom. The cartridge can then be rotated either by hand, but optionally mechanically to provide a vertical orientation. This process can be made automatic in that a sensor, located either on a cartridge device or the housing determining the presence of a sample, causes a signal to be sent to the cartridge, activating the means of rotation to the required orientation. The sensor can be linked via processor to a spirit level or the like so that current orientation of the cartridge and fluid connection is known.

Additionally or alternatively, vibration means can be included to cause movement of fluid in the condensing zone by vibration of the condensing zone.

In a further alternative embodiment, means are included to prevent saliva from a subject from reaching the condensing zone and so contaminating the breath sample. Saliva is known to have 10-100 times the hydrogen peroxide content than is present in the air from the lungs. Such a prevention means must be such as to not interfere with the normal breathing of the subject, often referred to as a Tidal Breathing technique. One option of the prevention means comprises a convoluted path, and optionally one or more valves.

The prevention means can be brought together on a common housing with the device 10, such that breath exiting the prevention means is directed onto the condensing zone 12. The prevention means, usually formed into a mouthpiece into which a patient breathes, is preferably replaceable once used, to improve the hygiene and accuracy of the analyser.

In a yet further embodiment means can also be included to prevent humidity from the ambient air from condensing in the condensing zone and contaminating the sample, primarily by dilution, also possibly by introducing air-borne contaminants. This is illustrated in FIGS. 12.

One of the potential sources of contamination of the exhaled breath condensate is the co-incidental condensing of humidity from the ambient air, which will be an uncontrolled process causing uncontrolled hydrogen peroxide concentrations. The valve system illustrated in FIGS. 12*a*-12*f* prevents the ambient air from readily making its way to the Peltier cooler and being condensed within the cartridge. Additionally, the mouth piece 120 allows the effective use of accessories to be used if required, such as: saliva traps, filters, flow restrictors and nose clips. Therefore, the analyser can be used in several modes of operation depending on whether or which accessories are used.

The use of valves and baffles ensures that the majority of the exhaled breath is now forced to pass within the vicinity of the cooled condensing zone of the cartridge, ensuring a good efficiency in condensing the exhaled breath vapour. The valved mouth piece can have one or more chambers within it, with chambers directly connected or connected via a valve. In the disclosed embodiment there are three chambers, with a valve between Chamber One 121 and Chamber Two 122, whilst Chamber Two 122 and Chamber Three 123 are in direct contact. In the illustrated embodiment, the mouth-piece 120 is intended to be secured, in use, to a housing by means of external lugs 128.

The logic of the valves is that all the valves are normally closed when the analyser is not in operation. Upon inhalation Valve Three 126 opens, whilst Valve One 124 and Valve Two 125 remain closed. Upon exhalation Valve Three 126 closes and Valves Two 125 and One 124 open. The analyser provides for the immediate analysis of exhaled breath condensate analytes, where the ambient air is precluded from the cartridge behind one or more normally closed valves. The device directing air into the lungs and from the lungs to the cartridge can have one or more chambers laid out either in series or parallel.

In use therefore, a user secures the mouth-piece 120 to a housing, via suitable fixing means. Means are provided to ensure that the mouth-piece 120 is securely in position, and that the Valve One 124 is in fluid connection with the condensing zone 12. The analyser is activated and a user places their mouth about the entry port 127 and commences to breathe normally. The exhaled breath passes through the chambers 121, 122, 123 respectively. The change of direction of around 90° on breath entering through the Valve Two 125 and leaving the mouth-piece via the Valve One 124 ensures that unwanted material exhaled by the user, or leaving the mouth of the user does not reach the cartridge device 10.

As an example of valves suitable for the present invention, diaphragm valves can be cited. Diaphragm valves are used such that when a user is inhaling one valve opens to allow air in, whilst the other is closed. Upon exhalation, the valve state is reversed.

The analyser is designed to ensure the efficient condensation of vapour from the breath by directing the exhaled breath across the surface of the cartridge's condensing zone. Chambers can be connected to one another directly or connected via valves. During the breath cycle the flow of air is controlled to allow air into the lungs, whilst not exposing the cartridge to the ambient air; subsequently upon exhalation the exhaled breath is led along a path where the breath is passed over the cold zone before venting to the ambient. The judicious use of valves means ambient air is precluded from directly reaching the cartridge when the analyser is either operational or non-operational, with the logic of the valves as shown in Table 1. Additionally, the analyser has one or more ports which allow for air/gas exchange between the user, the ambient air and the air within the analyser and device. These ports can be used in conjunction with accessories including saliva traps, flow constrictors and filters etc., allowing several modes of action. Lastly the analyser can be used in conjunction with a means to prevent the flow of air through the user's nasal passages so as to force a mode of breathing where air passes only through the mouth.

TABLE 1

| Operation | Valve Logic | Comments |
| --- | --- | --- |
| Inhalation | Valve Three: open<br>Valve Two: closed<br>Valve One: closed | This is to allow the user to inhale through the analyser whilst preventing the air that is being inhaled flowing over the condensing zone. |
| Exhalation | Valve Three: closed<br>Valve Two: open<br>Valve One: open | The valve logic means the exhaled breath has to follow a path where it flows within the vicinity of the cooled condensation zone on the cartridge leading to a more efficient condensation of the vapour within the exhaled breath. |

TABLE 1-continued

| Operation | Valve Logic | Comments |
|---|---|---|
| Not in Use | Valve Three: closed<br>Valve Two: closed<br>Valve One: closed | When not in use, all the valves are closed and therefore reduces the amount of ambient vapour that can be accidentally condensed within the analyser. |

In a still yet further embodiment of the analyser, the flow rate of the exhaled breath can be monitored, allowing a user or a supervising individual to allow the control of the flow rate or issue guidance. The sensor means for the flow rate may therefore be included within the device. The sensor thereby transmits real time data, which can provide visual or audio feedback, so that the breathing rate can be adjusted to stay within acceptable boundaries. Additionally, the breathing rate can be utilised as part of the diagnostic determination.

An exemplary analyser may have the following three modes of operation:

Mode One—Analyse a subject's status from one or more real-time signals including: breath exhalate carbon dioxide levels, breath water content, breath pressure, breath temperature; one or more of these signals are used to determine the status of the user, and/or their lung functionality.

Mode Two—Analyse a subject's status from a collected exhaled breath condensate, this measurement can be corrected for parameters such as breath exhalation profile, breath water content, breath carbon dioxide levels etc. For example, the carbon dioxide signal can be used to calculate the fractionated analyte concentration from the measured analyte concentration.

Mode Three—Analyse a subject's status by combining the two modes described above, so that a breath condensate can be reported within the context of the overall exhaled breath profile and breath gas analysis.

In a further exemplary embodiment, a mouthpiece employs an arrangement of baffles to minimise the chance of aerosol from the mouth reaching the condensation zone. In one arrangement air entering the mouthpiece encounters a first baffle which charges the air velocity by around 90°. A second baffle then causes an approximately 180° change of direction. In this manner large droplets from the mouth are caused to drop out of the airflow, allowing vapour from the lungs through.

The cartridge device is typically held, replaceably, within a housing to form an analyser, which housing includes features such as cooling, heating, processing means which can be used in co-operation with the cartridge device. A detection means can be present to indicate a cartridge device is correctly installed within a housing. The housing may comprise a cooling means, such as a Peltier plate, for cooling the cartridge to a suitable temperature for condensation. The cooling means may alternatively be part of the cartridge. Further, the analyser can be held inactive until both the cartridge is correctly in place and cooling has been properly achieved.

The analyser can combine any number of signals to determine a patient's status or to calibrate a signal. Additionally, the analyser can open and close valves in response to defined conditions being met, for example the collection of fractionated breath by triggering valve when carbon dioxide level criteria are met.

The analyser provided is light and portable so can be picked up and placed in front of the mouth, and can be operated without being physically tethered to a power supply or third-party device. To aid a user, a display can be provided to indicate that the analyser is ready for use. In order to enable use remote from a mains electrical power supply, a power pack can be included either mounted integrally or removably in the housing, or optionally or additionally as part of a cartridge device.

The analyser is designed to be used with tidal breathing for greater patient acceptance, relative to previous devices which would require forced air manoeuvres.

The analyser aims to perform all the necessary functions involved within the workflow of collecting and analysing the breath condensate without manual interference or intervention by a user or clinician. The analyser may have both real-time sensing and analysis of the breath and physical parameter associated with breathing. Optionally, the analyser can share data relating to a patient, and also include a comparator to determine directly any change in performance for a patient.

In one preferred embodiment the breath condensate film is directed immediately from the subject's mouth through a tortuous flow path to the fully integrated analyser (i.e. housing plus cartridge), where the breath is condensed into a breath film condensate upon a cooled zone. The resulting condensate film is immediately guided by a combination of capillary forces and gravity across a functionalised surface to a chamber. The film enters the chamber by following down the chamber's sides and filling the chamber from the bottom up. Finally, the condensate dissolves several salt patches; the dissolution of salt into the breath film condensate is electrically/electrochemically monitored and checked for the correct dissolution profile as part of onboard assay quality control. An incorrect profile is used to reject the cartridge.

One inventive concept relates to a single integrated cartridge device for condensing breath as a film and analysing analytes within the exhaled breath condensate film. The device performs all the necessary functions involved within the workflow of collecting and analysing the breath condensate without manual interference or intervention by a user such as a clinician. The device includes a least one temperature zone for breath condensation that is integrated with at least one sensing zone for measurement upon the condensate.

In a further embodiment, not illustrated, the condensation zone is incorporated into the housing and not into the cartridge device. The cartridge device, in this embodiment, is removably attachable to the housing, and, on attachment, becomes fluidly linked to the condensation zone, allowing condensed breath to flow into the cartridge device for analysis in the manner described above.

In the preferred embodiment of the apparatus the condensation zone is connected to the patient's mouth by a short tortuous flow path, designed to allow the passage of vapour from the lungs, and in particular, the alveolar part of the lung, whilst excluding aerosol from the mouth etc. Following condensation of exhaled breath, the film flows under the influence of gravity and capillary forces into a chamber, which is closed on five sides; the film flows down the sides of the chamber effectively filling the chamber from the bottom up.

Near the completion of filling the chamber the breath film condensate dissolves patches of salt, the salt is necessary for both fixing the potential at a silver/silver chloride reference electrode and for providing a relatively low impedance sample.

The invention claimed is:

1. An analyser for collecting and analysing a breath condensate, the analyser comprising a housing, the housing having a cooling means and, further, retaining a cartridge device comprising a condensation zone to condense exhaled breath from a subject, the cooling means being in cooling relationship with the condensation zone, the cartridge including one or more further discrete regions for detection of an analyte and measurement of the analyte, the cartridge further comprising a fluid path connecting the condensation zone to the or each discrete region, the housing including a mouth-piece having an entry port to enable a user to breathe into the mouth-piece, the mouth-piece comprising one or more fluid passages to direct breath entering the mouth-piece into the condensation zone, the mouth-piece further comprising an exit valve, and a plurality of chambers interposed between the entry port and exit valve to direct fluid flow from the entry port to the exit valve, the chambers being so configured to cause a change of 90 in the direction of fluid flow, wherein at least two chambers are separated by a one-way valve.

2. The analyser according to claim 1, wherein the cartridge is removably attachable to the housing.

3. The analyser according to claim 1, wherein the housing comprises a heating means to heat a reaction zone which itself forms part of the cartridge.

4. The analyser according to claim 3, wherein the heating means is arranged in the housing or as part of the cartridge.

5. The analyser according to claim 4, wherein there is an electrical connection between the housing and the cartridge.

6. The analyser according to claim 1, wherein the housing comprises a series of baffles to remove saliva aerosol from a vapour sample.

7. The analyser according to claim 6, wherein one or more baffles is provided in the mouth-piece.

8. The analyser according to claim 7, wherein a single baffle is provided in each of the mouth-piece, housing and the cartridge.

9. The analyser according to claim 1, wherein the housing comprises a valve system to provide at least two flow paths through the cartridge.

10. The analyser according to claim 1, wherein the housing and/or the cartridge comprises a flow rate sensor for measuring breath flow rate.

11. The analyser according to claim 1, wherein the housing and/or the cartridge comprises a carbon dioxide sensor.

12. The analyser according to claim 1, wherein the housing and/or the cartridge comprises one or more humidity/relative humidity sensors.

13. The analyser according to claim 1, wherein the housing and/or the cartridge comprises a pressure sensor for measuring breath pressure during exhalation or inhalation.

14. The analyser according to claim 1, wherein the housing and/or the cartridge comprises a temperature sensor for measuring breath temperature.

15. The analyser according to claim 1, wherein the housing comprises an electronic interface for providing information from one or more sensors to an external device and/or for receiving electrical energy from an external source.

16. The analyser according to claim 1, wherein the housing comprises a data processing unit.

17. The analyser according to claim 1, wherein the housing comprises an electronic interface for a removable data storage means, or via wire or wireless data transmission.

18. The analyser according to claim 1, wherein the housing comprises an audio output.

* * * * *